US007202089B2

(12) United States Patent
Kleinfeld

(10) Patent No.: US 7,202,089 B2
(45) Date of Patent: Apr. 10, 2007

(54) EARLY DIAGNOSIS OF STROKE

(76) Inventor: Alan Kleinfeld, 6777 Via Estrada, La Jolla, CA (US) 92037

( * ) Notice: Subject to any disclaimer, the term of this patent is extended or adjusted under 35 U.S.C. 154(b) by 517 days.

(21) Appl. No.: 10/243,565

(22) Filed: Sep. 13, 2002

(65) Prior Publication Data
US 2003/0054412 A1  Mar. 20, 2003

Related U.S. Application Data

(60) Provisional application No. 60/322,571, filed on Sep. 14, 2001.

(51) Int. Cl.
G01N 33/92 (2006.01)
(52) U.S. Cl. ............. 436/71; 435/968; 436/71; 436/172; 436/518
(58) Field of Classification Search ............ 435/7.8, 435/9.68; 436/518, 172
See application file for complete search history.

(56) References Cited

U.S. PATENT DOCUMENTS

| | | | |
|---|---|---|---|
| 4,071,413 A | 1/1978 | Takahashi et al. | |
| 4,369,250 A | 1/1983 | Gindler | |
| 5,225,329 A | 7/1993 | Marks | |
| 5,449,607 A | 9/1995 | Wilton | |
| 5,470,714 A | 11/1995 | Kleinfeld | |
| 5,496,735 A | 3/1996 | Schwertner | |
| 5,512,429 A | 4/1996 | Wilton | |
| 5,604,105 A | 2/1997 | Jackowski | |
| 5,914,112 A | 6/1999 | Bednar et al. | |
| 5,977,174 A * | 11/1999 | Bradley et al. | 514/549 |
| 6,210,976 B1 | 4/2001 | Sabbadini | |
| 6,264,960 B1 * | 7/2001 | Robins et al. | 424/400 |
| 6,444,432 B1 | 9/2002 | Kleinfeld | |
| 6,727,258 B2 * | 4/2004 | Baraldi | 514/260.1 |
| 6,750,030 B2 | 6/2004 | Kleinfeld | |
| 2004/0077017 A1 * | 4/2004 | Karlstrom et al. | 435/7.1 |

FOREIGN PATENT DOCUMENTS

| | | |
|---|---|---|
| EP | 1 043 587 B1 | 6/2003 |
| SU | 1270706 | 9/1981 |
| WO | WO 91/09310 | 6/1991 |
| WO | WO 93/08276 | 4/1993 |
| WO | WO 94/06014 | 3/1994 |
| WO | WO 98/57171 | 12/1998 |

OTHER PUBLICATIONS

Pelsers et al, Fatty acid-binding proteins as plasma markers of tissue injury, 2005, vol. 352, pp. 15-35.*

N. Bazán, et al. "Membrane Lipids in the Pathogenesis of Brain Edema: Phospholipids and Arachidonic Acid, the Earliest Membrane Components Changed at the Onset of Ischemia," *Advances in Neurology*, vol. 28: Brain Edema, Raven Press, New York, 1980, pp. 197-205.

N. Bazán, et al. "Effects of Ischemia and Electroconvulsive Shock on Free Fatty Acid Pool in the Brain," *Biochimica et Biophysica Acta*, 218, 1970, pp. 1-10.

M. Ikeda, et al. "Polyphosphoinositides as a Probably Source of Brain Free Fatty Acids Accumulated at the Onset of Ischemia," *Journal of Neurochemistry*, Raven Press, New York, 1986, pp. 123-132.

V. Kurien, "Serum-Free-Fatty-Acids After Acute Myocardial Infarction and Cerebral Vascular Occlusion," *The Lancet*, Jul. 16, 1966, pp. 122-127.

G. Richieri, et al. "Unbound Free Fatty Acid Levels in Human Serum," *Journal of Lipid Research*, vol. 36, 1995, pp. 229-240.

G. Richieri, et al., "Interactions of Long-Chain Fatty Acids and Albumin: Determination of Free Fatty Acid Levels Using the Flourescent Probe ADIFAB," *Biochemistry*, vol. 32, 1993, pp. 7574-7580.

G. Richieri, et al. "Kinetics of Fatty Acid Interactions with Fatty Acid Binding Proteins from Adipocyte, Heart, and Intestine," *The Journal of Biological Chemistry*, vol. 271, No. 19, May 10, 1996, pp. 11291-11300.

G. Richieri, et al. "The Measurement of Free Fatty Acid Concentration with the Fluorescent Probe ADIFAB: A Practical Guide for the Use of the ADIFAB Probe," *Molecular and Cellular Biochemistry*, 192: 1999, pp. 87-94.

G. Richieri, et al. "A Fluorescently Labeled Intestinal Fatty Acid Binding Protein," *The Journal of Biological Chemistry*, vol. 267, No. 33, Nov. 25, 1992, pp. 23495-23501.

B. Weinberger, et al. "Effects of Perinatal Hypoxia on Serum Unbound Free Fatty Acids and Lung Inflammatory Mediators," *Biology of the Neonate*, vol. 79, 2001, pp. 61-66.

Supplementary Partial European Search Report completed on Dec. 21, 2004 and issued to a related, foreign application.

(Continued)

Primary Examiner—Christopher R. Tate
Assistant Examiner—Deborah A. Davis
(74) Attorney, Agent, or Firm—Knobbe, Martens, Olson & Bear, LLP

(57) ABSTRACT

A method is described for the early detection of stroke which uses a reagent which includes a fluorescently modified fatty acid binding protein. A fluorescence difference is noted between the bound and unbound condition. Elevated levels of unbound free fatty acids from blood are used as indicators of stroke.

15 Claims, No Drawings

OTHER PUBLICATIONS

Davies, et al. "Perioperative Variability of Binding of Lidocaine, Quinidine, and Propranolol After Cardiac Operations," *Journal of Thoracic and Cardiovascular Surgery*, vol. 96, No. 4, pp. 634-641, Oct. 1998.

Ford, et al. "Use of Serum Markers of Myocardial Injury for the Early Diagnosis of Acute Myocardial Infarction," *ACC Current Journal Review*, vol. 5, No. 3, pp. 86-89, May/Jun. 1996.

Kleinfeld, et al. "Increases in Serum Unbound Free Fatty Acid Levels Following Coronary Angioplasty," *American Journal of Cardiology*, vol. 78, No. 12, pp. 1350-1354, Dec. 15, 1996.

Glatz, et al. "Fatty-Acid-Binding Protein as a Plasma Marker for the Estimation of Myocardial Infarct Size in Humans," *BR Heart J*, vol. 71, pp. 135-140, 1994.

Patel, et al. "Serum Levels of Unbound Free Fatty Acids I: Normative Data in Term Newborn Infants," *Journal of American College of Nutrition*, vol. 16, No. 1, pp. 81-84, 1997.

Peuhkurinen, et al. "Changes in Myocardial Energy Metabolism in Elective Coronary Angioplasty," *Cardiovascular Research*, vol. 25, pp. 158-163, 1991.

Richieri, et al. "Equilibrium Constants for the Binding of Fatty Acids with Fatty Acid-Binding Proteins from Adipocyte, Intestine, Heart, and Liver Measured with the Fluorescent Probe ADIFAB," *The Journal of Biological Chemistry*, vol. 269, No. 39, pp. 23918-23930, Sep. 30, 1994.

Richieri, et al. "Thermodynamic and Kinetic Properties of Fatty Acid Interactions with Rat Liver Fatty Acid-Binding Protein," *The Journal of Biological Chemistry*, vol. 271, No. 49, pp. 31068-31074, Dec. 6, 1996.

Richieri, et al. "Unbound Free Fatty Acid Levels in Human Serum," *Journal of Lipid Research*, vol. 36, No. 2, pp. 229-240, Feb. 1995.

Richieri, et al. "A Fluorescently Labeled Intestinal Fatty Acid Binding Protein. Interactions with Fatty Acids and its Use in Monitoring Free Fatty Acids," *The Journal of Biological Chemistry*, vol. 267, No. 33, pp. 23495-23501, Nov. 25, 1992.

Richieri, et al. "Kinetics of Fatty Acid Interactions with Fatty Acid Binding Proteins from Adipocyte, Heart, and Intestine," *The Journal of Biological Chemistry*, vol. 271, No. 19, pp. 11291-11300, May 10, 1996.

Ruben, et al. "Serum Levels of Unbound Free Fatty Acids II: The Effect of Intralipid Administration in Premature Infants," *Journal of the American College of Nutrition*, vol. 16, No. 1, pp. 85-87, 1997.

Samanta, et al. "Possible Physiological Role of Myocardial Fatty Acid Binding Protein in Phospholipid Biosynthesis," *Journal of Lipid Mediators*, vol. 1, pp. 243-255, 1989.

Samanta, et a. "Free Radical Scavenging by Myocardial Fatty Acid Binding Protein," *Free Radical Research Communications*, vol. 7, No. 2, pp. 73-82, 1989.

She, et al. "The Substrate Specificities of Four Different Lysophospholipases as Determined by a Novel Fluorescence Assay," *Biochem J.*, vol. 298, pp. 23-29, 1994.

Victor, et al. "Myocardial Tissue Free Fatty Acids," *Journal of Molecular and Cellular Cardiology*, vol. 16, No. 8, pp. 709-721, Aug. 1984.

*Textbook of Cardiovascular Medicine*, Eric J. Topol, Editor; Lippincott-Raven Publishers, Philadelphia, PA, 1998. Chapter 16, Harvey D. White, "Unstable Angina—Ischemic Syndromes." pp. 365-393.

Brown, et al., "Fatty Acids and the Inhibition of Mitogen-Induced Lymphocyte Transformation by Leukemic Serum," *The Journal of Immunology*, vol. 131, No. 2, pp. 1011-1016, Aug. 1983.

Butko, et al. "Acidic Phospholipids Strikingly Potentiate Sterol Carrier Protein 2 Mediated Intermembrane Sterol Transfer," *Biochemistry*, vol. 29, pp. 4070-4077, 1990.

International Search Report, dated Mar. 13, 2003, issued in relation to a related, pending foreign application.

Bansal, et al. "Stroke During Pregnancy and Puerperium in Young Females Below the Age of 40 Years as a Result of Cerebral Venous/Venous Sinus Thrombosis," *Japanese Heart Journal*, vol. 21, No. 2, pp. 171-183, Mar. 1980.

Ageeva, et al. "Structural and Functional Characteristics of Red Cell Membranes in Patients with Ischemic Stroke and Dyscirculatory Encephalopathy," Zhurnal Nevrologii I Psikhiatrii Imeni SS Korsakova, vol. 94, No. 1, pp. 6-8, 1994. English Abstract.

Imre, et al. "Increased Proportion of Docosahexanoic Acid and High Lipid Peroxidation Capacity in Erythrocytes of Stroke Patients," *Stroke*, vol. 25, No. 12, pp. 2416-2420, 1994.

Supplementary European Search Report completed on Aug. 12, 2004 and issued to a related foreign application.

\* cited by examiner

EARLY DIAGNOSIS OF STROKE

RELATED APPLICATIONS

This application claims the priority of Provisional Application No. 60/322,571, filed Sep. 14, 2001 which is incorporated herein by reference.

BACKGROUND OF THE INVENTION

1. Field of the Invention

This invention relates to the diagnosis of stroke by the measurement of unbound free fatty acids in body fluids such as whole blood, plasma and serum.

2. Description of the Related Art

Stroke is defined as the interruption of blood flow to brain tissue. This can be an interruption to a particular portion of the brain or a reduction of virtually all flow when, for example pumping of the blood by the heart fails completely. More frequently, stroke occurs when flow to a particular part of the brain is interrupted by the blockage or rupture of a blood vessel that serves the brain. Blockage of a vessel, for example, through an embolism or the formation of a thrombus, generally in an artery that supplies blood to the brain is known as an ischemic stroke. The rupture of a blood vessel within the brain, generally through an aneurysm, is known as a hemorrhagic stroke.

In the case of an ischemic stroke, the interruption of blood flow may be temporary; this is known as a transient ischemic event (TIA). In this case, the patient often suffers no clinically or measurable deleterious consequences but is at high risk for subsequent strokes. In contrast, patients whose blockage does not resolve within a few hours suffer permanent damage, often resulting in death. This is a consequence of the death of brain cells (tissue) that were normally supplied with nutrients and oxygen by the now occluded vessel. This death or infarct of the tissue can be detected by computer aided tomography (CT scan) or by nuclear magnetic resonance imaging (MRI) but only many hours after the stroke (the first symptoms) started. In the case of hemorrhage, the brain begins to fill with blood resulting in the destruction of tissue.

Stroke is the third leading cause of death in developed countries. New cases of stroke affect approximately 750,000 individuals every year in the United States alone. The estimated costs for treatment and lost productivity as a result of death and morbidity from stroke are about $40 billion dollars in the U.S. The only effective treatment available for stroke is the delivery of thrombolytic agents such as tissue plasminogen activator (t-PA) that destroy the clot by enzymatically cleaving proteins that help form the clot. T-PA can only be given within 3 hours of the first symptom because of deleterious effects (hemorrhage) if used too late. Moreover, t-PA can only be used in ischemic stroke; its use in hemorrhagic stroke generally leads to death.

Thus, thrombolytic therapy can only be used if diagnosed quickly and only if hemorrhagic stroke is ruled out. Current methods of diagnosis rely virtually entirely on clinical presentation, generally the opinion of the emergency physician. If the physician suspects stroke and thinks that the patient may be a candidate for thrombolytic therapy, then the patient must quickly undergo a CT scan to rule out hemorrhage (which the CT scan can detect at an early stage). Generally, because of the time required for these decisions and procedures, very few potentially eligible patients receive thrombolytic therapy.

Consequently, there is a long felt need for availability of a simple and rapid blood test that would determine the presence or absence of ischemic stroke in an individual and could distinguish between ischemic and hemorrhagic stroke. The diagnostic method described here, measurement of unbound free fatty acid in body fluids such as blood, serum or plasma, involves a simple, inexpensive, virtually instantaneous, and readily accessible measurement that has high potential for revealing the ischemic event.

SUMMARY OF THE INVENTION

The present inventor has found that levels of unbound free fatty acid are elevated during stroke. This observation provides a convenient way to detect and diagnose stroke and possibly to differentiate ischemic stroke from other conditions which may present with similar symptoms such as hemorrhagic stroke, migraine and seizure.

In one embodiment, a method of detecting stroke in a mammal is described which includes the steps of:

providing a body fluid sample from a mammal exhibiting symptoms consistent with ischemic stroke;

mixing the sample with an aqueous solution and with a reagent which includes a fatty acid binding protein labeled with a fluorescent moiety, wherein the reagent exhibits a first fluorescence in an aqueous solution and a measurably different second fluorescence in an aqueous solution when the fatty acid binding protein is bound to a fatty acid; and measuring the second fluorescence after the body fluid sample is mixed with the aqueous solution and the reagent to determine a concentration of unbound free fatty acid in the body fluid sample. In a preferred embodiment, the body fluid is from the group including whole blood, serum and plasma.

In another embodiment, a method to monitor the course of stroke therapies in a patient using body fluid levels of unbound free fatty acids is described which includes the steps of:

measuring unbound free fatty acid levels in a body fluid sample from said patient at different times throughout the stroke therapy;

comparing the measured level of unbound free fatty acid to a threshold level of unbound free fatty acid, wherein the threshold level is determined from measuring unbound free fatty acid in body fluid of a normal population that is asymptomatic for stroke; and determining whether the unbound free fatty acid level from the patient's body fluid samples at any given time point during the stroke therapy is trending towards the threshold level of unbound free fatty acids from the normal population indicating success of the stroke therapy.

In another embodiment, a method is described for determining the presence of stroke in a patient presenting with symptoms consistent with stroke including the steps of:

measuring unbound free fatty acid levels in a body fluid sample from the patient;

comparing the measured level of unbound free fatty acid to a threshold level of unbound free fatty acid, wherein the threshold level is determined from measuring unbound free fatty acid in body fluid of a normal population that does not have stroke; and determining whether the unbound free fatty acid level from the patient's body fluid sample is elevated relative to the threshold level of unbound free fatty acids from the normal population, wherein the relative elevation indicates an increased risk for stroke. In one embodiment, the body fluid may be blood, serum, or plasma.

In one embodiment, the measuring step may further include the steps of:

mixing the body fluid sample with an aqueous solution and with a reagent which includes a fatty acid binding protein labeled with a fluorescent moiety, wherein the reagent exhibits a first fluorescence in an aqueous solution and a measurably different second fluorescence in an aqueous solution when the fatty acid binding protein is bound to a fatty acid; and measuring the second fluorescence after the body fluid sample is mixed with the aqueous solution and the reagent to determine a concentration of unbound free fatty acid in the body fluid sample. In one embodiment, the measuring step of the second fluorescence is performed at a wavelength that differs from a wavelength at which the reagent exhibits the first fluorescence. In a preferred embodiment, the wavelength for measuring the second fluorescence is about 420 nm to about 460 nm, and the wavelength at which the reagent exhibits the first fluorescence is about 495 nm to about 560 nm.

In a preferred embodiment, the fatty acid binding protein is a rat intestinal fatty acid binding protein, a human adipocyte fatty acid binding protein, or a rat heart fatty acid binding protein. The fluorescent moiety may be selected from the group including but not limited to acrylodan, danzyl aziridine, 4-[N-[(2-iodoacetoxy)ethyl]-N-methylamino]-7-nitrobenz-2-oxa- 1,3-diazole ester (IANBDE), or 4-[N-[(2-iodoacetoxy)ethyl]-N-methylamino]-7-nitrobenz-2-oxa-1,3-diazole (IANBDA).

In a preferred embodiment, the reagent in the mixing and measuring steps is a fatty acid binding protein labeled with acrylodan, and the fatty acid binding protein is a mutant protein including, but not limited to, a rat intestinal fatty acid binding protein having a cysteine at residue 27, 81, 82, or 84, or an alanine at residue 72, or a rat heart fatty acid binding protein having a lysine at residue 27. In a most preferred embodiment, the reagent in the mixing and measuring steps is a rat intestinal fatty acid binding protein labeled with acrylodan. In an alternate preferred embodiment, the reagent is a rat intestinal fatty acid binding protein labeled with acrylodan and having an alanine at residue 72.

In one embodiment, the concentration of the unbound free fatty acid which is indicative of stroke is greater than 2 standard deviation units above an average value of the concentration of the unbound free fatty acid determined from a non-ischemic population. In another embodiment, the concentration of the unbound free fatty acid indicative of stroke is greater than about twice an average value of the concentration of the unbound free fatty acid determined from a non-ischemic population.

In one embodiment, the method may further include the steps of:

measuring total free fatty acid and albumin in the blood sample; and determining a ratio of the total free fatty acid and the albumin.

Other proteins that bind fatty acids may also be used. In one embodiment, the method of determining the presence of stroke in a patient presenting with symptoms consistent with stroke may include the steps of:

mixing the body fluid sample with an aqueous solution and with a reagent comprising albumin labeled with a fluorescent moiety which may be either of 7-hydroxycoumarin or anthraniloyl, for example, wherein the reagent exhibits a first fluorescence in an aqueous solution and a measurably different second fluorescence in an aqueous solution when albumin is bound to a fatty acid; and measuring the second fluorescence after the body fluid sample is mixed with the aqueous solution and the reagent to determine a concentration of unbound free fatty acid in the body fluid sample.

In one embodiment, a method is described for identification of patients at high risk for hemorrhage which includes the steps of:

measuring unbound free fatty acid levels in a body fluid sample from the patient;

comparing the measured level of unbound free fatty acid to a threshold level of unbound free fatty acid, wherein the threshold level is determined from measuring unbound free fatty acid in body fluid of a normal population that does not have ischemia; and determining whether the unbound free fatty acid level from the patient's body fluid sample is elevated relative to the threshold level of unbound free fatty acids from the normal population, wherein the relative elevation indicates an increased risk for hemorrhage.

In another embodiment, a method of identifying patients at high risk for mortality within three years after a stroke is described which includes the steps of:

measuring unbound free fatty acid levels in a body fluid sample from the patient;

comparing the measured level of unbound free fatty acid to a threshold level of unbound free fatty acid, wherein the threshold level is determined from measuring unbound or water-soluble free fatty acid in body fluid of a normal population that does not have stroke; and determining whether the unbound free fatty acid level from the patient's body fluid sample is elevated relative to the threshold level of unbound free fatty acids from the normal population, wherein the relative elevation indicates an increased risk for mortality within three years after a stroke.

In another embodiment a method is described for diagnosing ischemic stroke, which includes the steps of:

identifying a patient presenting symptomology consistent with ischemic stroke;

obtaining a body fluid sample from the patient;

measuring a level of unbound free fatty acid in the sample; and ascertaining whether the measured level of unbound free fatty acid is sufficiently elevated to be indicative of ischemic stroke. In a preferred embodiment, thrombolytic therapy is then administered to the patient when the measured level of unbound free fatty acid is indicative of ischemic stroke.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

The present invention describes the diagnosis and monitoring of stroke. In one embodiment, stroke is diagnosed or the course of a stroke treatment is monitored by measurement of a lipid component such as a fatty acid. Total fatty acids may be determined by methods well known in the art such as taught in U.S. Pat. No. 4,071,413, U.S. Pat. No. 5,512,429, U.S. Pat. No. 5,449,607, and U.S. Pat. No. 4,369,250 all of which are incorporated herein by reference.

Levels of total fatty acid obtained by these methods may be compared with levels obtained from normal individuals in order to detect an ischemic condition in an individual. In a preferred embodiment, a ratio of total fatty acid to albumin is determined and compared with a normal population.

In another embodiment, unbound free fatty acid levels are measured in a bodily fluid as described below. Preferably, the unbound free fatty acids are measured in a bodily fluid such as cerebral spinal fluid, interstitial fluid, blood, serum, plasma, urine, saliva, lymph, gastric juices, or bile. Unbound free fatty acids ($FFA_u$) are the portion of free fatty acids soluble in the aqueous phase. In preferred embodiments, the fluid used for the test sample is taken from cerebral spinal fluid, blood, plasma or serum. In most body fluids free fatty acid (FFA) is mostly bound to proteins, for example, albumin, and membranes but a significant minority is unbound ($FFA_u$) and soluble in the aqueous phase. $FFA_u$ are also referred to as water-soluble free fatty acids.

The present methods may advantageously be applied to selected patient populations. Thus, for example, samples of a bodily fluid in which $FFA_u$ may be present may be obtained from patients presenting with symptoms consistent with ischemic stroke, or patients with symptoms indicating neurological dysfunction. The method of the present invention may then be used, for example, to distinguish between symptomology due to ischemic stroke and symptomology due to other conditions, such as seizure, hemorrhagic stroke, migraine, and the like. Symptoms of stroke are well known in the medical community, and include partial or full paralysis, speech impairment, befuddlement, numbness or weakness in a limb, particularly on one side of the body, sudden loss or impairment of vision in one or both eyes, severe headache, loss of balance or other motor skills, and dizziness.

Another aspect of the present invention is the combination of the diagnostic steps discussed herein, which indicate whether a patient has had an ischemic stroke, with stroke-related therapy. One type of such therapy that can be used in the present invention is thrombolytic therapy (such as tPA or streptokinase). Preferably, such therapy is administered within a short time of the ischemic stroke event, and is advantageously administered within 3, 2, or more preferably 1 hour of the assay step that reveals levels of $FFA_u$ that are indicative of ischemic stroke.

Any assay that provides an indication of the level of $FFA_u$ in body fluid relative to an asymptomatic population may be used in the diagnostic method described. Preferably a threshold value is determined from a normal population that does not have stroke. In one embodiment, the threshold value is a concentration of $FFA_u$ in a body fluid that is significantly higher than the concentration of $FFA_u$ in the body fluid of a control population that does not have stroke. In one embodiment, the threshold value is a concentration of $FFA_u$ in a body fluid that is at least about two standard deviations greater than an average concentration of $FFA_u$ in a body fluid of a control population that does not have stroke. In another embodiment, the threshold concentration of $FFA_u$ in a body fluid is at least about two-fold greater than an average concentration of $FFA_u$ in a body fluid of a control population that does not have stroke.

In one embodiment, the present invention uses a fluorescently-labeled fatty acid binding protein (FABP) to measure an increased amount of unbound free fatty acid ($FFA_u$) in blood, serum or plasma samples associated with stroke by quantitatively detecting a shift in fluorescence associated with binding of a $FFA_u$ molecule to the fluorescently-labeled FABP. This invention utilizes the method substantially as described in U.S. Pat. No. 5,470,714, which is incorporated herein by reference. Alternatively, any other suitable label can be used that is capable of indicating the binding of FABP to $FFA_u$. A wide variety of assay formats and labeling technologies are known, and in at least some aspects of the present invention, the particular label or assay format is not critical, but rather any suitable assay format and label known in the art can be used.

A variety of FABP and fluorescent labels can be used in detecting levels of $FFA^u$ in body fluids such as blood, serum or plasma indicative of stroke. These include, for example, rat intestinal FABP (I-FABP), human adipocyte FABP (A-FABP) and rat heart FABP (H-FABP). Site-specific mutant forms of these FABP, in which one or more amino acid residues have been altered (inserted, deleted and/or substituted) are also useful in the method and include, for example, substitutions of Cys in I-FABP at positions 27, 81, 82, 84, an Ala substitution at residue 72 of I-FABP, and a Lys substitution at residue 27 of H-FABP.

The FABP molecules may be fluorescently-labeled using a variety of known labels including but not limited to acrylodan, danzyl aziridine, 4-[N-[(2-iodoacetoxy)ethyl]-N-methylamino]-7-nitrobenz-2-oxa-1,3-diazole ester (IAN-BDE), and 4-[N-[(2-iodoacetoxy)ethyl]-N-methylamino-7-nitrobenz-2-oxa-1,3-diazole (IANBDA). Other proteins that bind FFA and that change their fluorescence upon FFA binding may also be used including, but not limited to, albumin. In a preferred embodiment, albumin has a fluorescent label such as 7-hydroxycoumarin or anthraniloyl. Any label may be used in the practice of the invention as long as a measurable difference may be detected upon binding of a free fatty acid. For example, a difference in wavelength or in signal intensity may be monitored. Further examples of labels which may be used include, but are not limited to, chromophores which produce a change in absorbance or optical activity and spin labels which change is detectable by electron spin resonance.

In a preferred embodiment, a fluorescently-labeled FABP is acrylodan-derived recombinant rat intestinal fatty acid binding protein (referred to as ADIFAB). Derivatization with acrylodan was performed using known methods substantially as previously described (U.S. Pat. No. 5,470,714 & Richieri, G. V, et al., J. Biol. Chem., (1992) 276: 23495–23501), and ADIFAB is commercially available (FFA Sciences LLC, San Diego, Calif. ). Concentrations of $FFA_u$ can be determined by the binding of the $FFA_u$ to the fluorescently labeled fatty acid binding protein (FABP). A different fluorescence is exhibited when no FFA is bound to the fluorescently-labeled FABP. The concentration of $FFA_u$ can be determined from the fluorescence difference. The wavelength emitted by the fluorescently-labeled FABP depends upon the label and protein used. In one embodiment, the protein is either I-FABP or I-FABP with a substitution of Ala for Leu at position 72 where the label is acrylodan. These species are referred to as ADIFAB and ADIFAB2, respectively. The binding affinities of ADIFAB2 have been found to be about 10-fold greater than ADIFAB. The wavelengths at the maximum intensities emitted by these fluorescently-labeled I-FABP's in the absence of FFA is about 420 to 440 nm. The emission wavelengths at the maximum intensities for the FFA bound to the fluorescently-labeled I-FABP is about 495 to 580 nm. It will be understood that those skilled in the art can readily substitute other fluorescently-labeled FABP in the disclosed assay.

The assay for determination of $FFA_u$ levels in aqueous samples measures the intensity of a shift in fluorescence from a first wavelength, at which the derivatized FABP fluoresces when no FFA is bound, to a second wavelength, at which the derivatized FABP fluoresces when a molecule of FFA is bound, and the concentration of $FFA_u$ is then determined from the ratio ("R" value) of the two intensities of fluorescence wavelengths as described in U.S. Pat. No. 5,470,714 and Richieri, et al. (1995) J. Lipid Research, vol. 36: pages 229–240, both of which are incorporated herein by reference. Briefly, the ratio is calculated using the following formula:

$$R = \frac{I(1) - I(1)blank}{I(2) - I(2)blank}$$

wherein, I(1) and I(1)blank are the measured fluorescence intensities for a sample containing ADIFAB or ADIFAB2 and a blank sample containing all reagents except ADIFAB or ADIFAB2, respectively at wavelength "1"; and 1(2) and I(2)blank are the corresponding fluorescence intensities at wavelength "2". For ADIFAB, wavelength "1" is in preferably (but not absolutely) in the range of 495 and 515 nm and wavelength "2" is in the range from 422 to 442 nm. Measurements of fluorescence intensities may be obtained using standard techniques. As recognized by those skilled in the art, under appropriate conditions, the blank intensities in the above equation can be neglected.

Quantitative detection of levels of blood, serum or plasma $FFA_u$ that are elevated over blood, serum or plasma $FFA_u$ levels found in normal healthy individuals can be used to diagnose stroke. In one embodiment, stroke is indicated by a concentration of $FFA_u$ in a blood, serum, or plasma sample that is significantly higher than the concentration of $FFA_u$ in a blood, serum, or plasma sample of a control population that does not have stroke. In one embodiment, stroke is detected by levels of $FFA_u$ in blood, serum or plasma that exceed the average normal levels of $FFA_u$ in blood or serum or plasma by about 2 standard deviations. In another embodiment, $FFA_u$ levels which are two-fold greater than an average concentration of $FFA_u$ in a control population are indicative of stroke. Elevated levels of $FFA_u$ in blood, serum or plasma which are considerably higher may also be detected.

The diagnostic method of the present invention is based on the discovery that patients experiencing stroke have elevated levels of $FFA_u$ in body fluids such as blood, serum or plasma compared to normal levels of blood, serum or plasma $FFA_u$ in healthy individuals. While the diagnostic method may be carried out at any time, preferably, the test is carried out within 24 hours of the ischemic event. More preferably, the test is carried out within 10 hours of the ischemic event. Most preferably, the test is carried out within 3 hours of the ischemic event so that treatment may be initiated. Many treatments for ischemic conditions such as cardiac ischemia must be initiated quickly (within hours) in order to be effective. On the other hand, treatment without a correct diagnosis can be most deleterious to the patient. For example, initiation of thrombolytic therapy in the case of a hemorrhagic stroke can lead to death.

The test may be used to distinguish between ischemic stroke and other conditions such as migraine, seizure and hemorrhagic stroke. At the very least, this test will alert medical personnel that the patient is suffering from stroke. Thus, a CT or MRI scan could be more quickly initiated, shortening the time to thrombolytic therapy. This alert could happen even in the ambulance because the test can be easily administered by EMT personnel. Moreover, having the test done in an ambulance would be especially beneficial for patients that are distant from a facility with the necessary staff and equipment for treating stroke because the ambulance would be directed to the appropriate facility based on this test where appropriate therapy can be initiated. In the case of ischemic stroke, this therapy might include administration of thrombolytic agents such as t-PA. The use of t-PA is contraindicated in hemorrhagic stroke as its use generally leads to death.

EXAMPLE 1

Assay of $FFA_u$ in a Blood Sample

Briefly, the $FFA_u$ assay and determinations were performed as follows. Blood samples were diluted 100-fold in buffer (20 mM N-2-hydroxyethyl-piperazine-N'-2-ethane sulfonic acid (HEPES), 150 mM NaCl, 5 mM KCl and 1 mM $Na_2HPO_4$, adjusted to pH 7.4), yielding a serum albumin concentration of about 6 µM. A solution of fatty acid-free albumin plus ADIFAB or ADIFAB2 was the negative control. For each donor, two aliquots of serum were prepared: one "background" or "blank" sample of 1% serum and one "experimental" sample of 1% serum plus ADIFAB or ADIFAB2. The negative control, blank and experimental samples were measured at 22° C. or 37° C.

For each sample, multiple measurements of pairs of intensities were collected at about 432 nm and 505 nm, for ADIFAB and about 450 and 550 for ADIFAB2 and R values were determined after subtraction of the intensities of the blank sample. At least two separate measurements were done on different days for each serum sample and the mean values and standard deviations of $FFA_u$ concentrations were determined. To determine the probabilities of a difference between sets of measures, differences in means were evaluated using Student's t test, where a p value of less than 0.05 was considered significant.

EXAMPLE 2

[$FFA_u$] are Elevated in Patients Presenting with Stroke Symptoms in an Emergency Room Setting Blood samples were obtained from 39 patients admitted to the emergency department of a hospital at the time of admission and at several later time periods over the next several days. Unbound free fatty acid ($FFA_u$) levels were measured using a fluorescently modified fatty acid binding protein as described in U.S. Pat. No. 5,470,714. Both $FFA_u$ levels and creatine kinase (CK-MB) levels were measured in each sample. One patient was eventually diagnosed with stroke. $FFA_u$ values were found to be more than 2 times greater than normal levels during this period while CK-MB values were all in the normal range.

EXAMPLE 3

[$FFA_u$] are Elevated in a Rat Model of Focal Cerebral Ischemia

A rat model is used to monitor plasma $FFA_u$ levels associated with focal cerebral ischemia. Reversible focal cerebral ischemia of the left Middle Cerebral Artery (MCA) is induced by intraluminal occlusion as described in Jackson-Friedman, et al. (1997) Neurology vol. 147: pages 346–352. Plasma is sampled from the peripheral circulation. Adult rats are anesthetized. A 4-0 nylon suture (heat-blunted tip) is inserted in the common carotid artery and advanced via the internal carotid artery so that the tip reaches the anterior cerebral artery, thus occluding the origin of the MCA without entering its lumen. The free, proximal end of the suture filament is exposed externally after closing the arteriotomy. At specified times, the filament is pulled back, thereby restoring blood flow into the MCA. Approximately 0.1 ml blood is drawn at various times before and after occlusion. The blood samples are drawn into heparanized syringes containing buffered saline and placed immediately on ice to minimize hemolysis. The diluted blood is centrifuged and the plasma, diluted to 1%, is used to determine $FFA_u$ using ADIFAB2 at 22° C., essentially as described for ADIFAB in Richieri et al. (1999) Mol. Cell Biochem. vol. 192, pages 87–94.

Briefly, ADIFAB2 was obtained as follows. First, a restriction fragment, carrying the $Ala^{72}$ mutation and appropriate complementary ends, was substituted for the wild-type restriction fragment spanning the SalI site at position 211 in the I-FABP cDNA sequence (Alpers, et al. (1984) Proc. Natl. Acad. Sci U.S.A. 81: 313–317) and a PmeI site at position 291, which was introduced by site-specific mutagenesis. The mutated restriction fragment was constructed by annealing partially complementary synthetic oligonucleotides carrying the desired sequence, "filling in" single-stranded regions with the DNA polymerase Klenow fragment, and digesting with SalI and PmeI to give the appropriate termini. The $Ala^{72}$ substituted I-FABP cDNA was inserted into the pET11 vector and was expressed in the BL21(DE3) strain. The mutant I-FABP was purified essentially by the method of Lowe, et al. (Lowe, et al. (1987) J. Biol. Chem. 262: pages 5931–5937) and yielded about 100 mg of purified protein per liter of *Escherichia coli* culture. Acrylodan derivatization was done essentially as described previously for ADIFAB (see U.S. Pat. No. 5,470,714, incorporated herein by reference). Lipidex-5000 chromatography was used to remove free acrylodan.

The fluorescence properties of the acrylodan-derivatized Leu72→ Ala I-FABP (ADIFAB2) are significantly different than ADIFAB's. The positions of the emission maxima occur at longer wavelengths, about 440 nm for apo-ADIFAB2 and about 550 nm for holo-ADIFAB2, compared to about 432 and 505 nm for ADIFAB, and the optimal excitation wavelength is at about 375 nm for ADIFAB2 compared to about 386 nm for ADIFAB. Furthermore, the parameters that define the equilibrium binding properties $R_0$, $R_{max}$, and Q (see U.S. Pat. No. 5,470,714), are also significantly different for ADIFAB2 and, in contrast to ADIFAB, the values of these parameters are fatty acid and temperature dependent. Thus for 440 nm and 550 nm and oleate, $R_{max}$ and Q range between 1.6 and 2.5, and between 7.5 and 12, respectively, for temperatures between 10 and 37 ° C. and these values are all approximately 10% higher for palmitate and stearate.

Measurements are done using animals exposed to reversible MCA occlusions for times between about 15 minutes and 2 hours. Blood samples are drawn just before surgery, at the close of the wound and then at various times after surgery (eg. 1, 2, 3, 4 and 24 h). The time courses of the $[FFA_u]$ for the different occlusions are averaged. $[FFA_u]$ levels increase and peak at about 1–2 hours and then decrease gradually over the next 24 hours when they return to baseline. Levels of $FFA_u$ elevate quickly after occlusion and remain elevated for more than 4 hours. This behavior is important because the only treatment for an ischemic stroke is the administration of thrombolytic drugs such as tissue plasminogen activator (t-PA), which must be given within 3 hours of the initial symptoms. Moreover, the earlier t-PA can be administered the greater the therapeutic value. Rapid elevation of $FFA_u$ levels following the ischemic event provides an ideal diagnostic window.

EXAMPLE 4

Levels of FFAu Do not Remain Elevated in a Rat Model of Hemorrhagic Stroke

A major problem in diagnosing ischemic stroke is that patients suffering from non-cerebral ischemic syndromes often present with symptoms that mimic stroke. Chief among these "stroke mimics" are hemorrhagic stroke and seizure. A mistaken diagnosis in the case of a hemorrhagic event is particularly serious because t-PA might be fatal for such a patient.

A possible model for hemorrhagic stroke is obtained by injecting 100–200 ml of rat blood into the caudate nucleus. The hemorrhage (hematoma) model reveals a very rapid spike in $[FFA_u]$ at the time of injection (0) followed by a return to baseline in 1–2 hours. The $[FFA_u]$ time course decreases from time zero and by 2 hours is within 30% of baseline.

EXAMPLE 5

Levels of FFAu are not Elevated During Seizure

A rat model for seizure is obtained by infusion of biculline into the caudate nucleus which induces seizures The time course of $[FFA_u]$ in the seizure model reveals virtually no change from base line over 24 hours.

EXAMPLE 6

The Stroke-Mediated Increase in Plasma FFA Results from Adipose Tissue Lipolysis It has long been known that cerebral ischemia, induced in animals, results in the accumulation of FFA within cerebral tissue. Such determinations require harvesting of brain tissue and organic extraction to isolate the lipid components of the tissue. The FFA content of the ischemic brain has been found to increase within minutes of the induction of ischemia and eventually may increase by as much as 8 fold (in complete ischemia) relative to control tissue. It might therefore seem that an increase in plasma FFA would follow as an obvious consequence of the increase in FFA content of the ischemic brain. However the absolute amount of FFA generated even in complete ischemia (decapitation) is too small, in comparison with plasma levels of FFA to increase $[FFA_u]$ significantly. For example, in complete ischemia about 0.8 μmoles of FFA accumulate in the rat brain. The quantity of FFA in plasma following, much less profound, reversible cerebral ischemia is about 100 times greater.

The only tissue with sufficient capacity to generate the large quantities of FFA observed in cerebral ischemia is adipose tissue. Our studies indicate that within minutes of cerebral ischemia the brain releases one or more activators of adipose lipolysis. At least 2 such activators are released upon cerebral ischemia, norephinephrine and $TN_F\alpha$. $[FFA_u]$ and $TNF_\alpha$ in the same blood specimens are drawn in a reversible 2 hour occlusion in the rat stroke model (Example 2). Both quantities are elevated and follow the same time course.

EXAMPLE 7

[FFA$_u$] are Elevated Early in Human Patients Presenting with Cerebral Ischemia Measurement of [FFA$_u$] in stroke patients would allow a rapid and sensitive indicator of ischemic stroke and would allow such patients to be distinguished from stroke mimic.

Results of measurements of [FFA$_u$] in the population of nominally healthy human subjects (normals) were reported previously in Richieri et al. (1995) J. Lipid Res. vol. 36: pages 229–240. These measurements were done at 37° C. using the first fluorescent probe of FFA$_u$, ADIFAB. The results of these measurements revealed an average and standard deviation of 7.5 nM and 2.5 nM, respectively. Measurements of [FFA$_u$] at 22° C. using the ADIFAB2 probe (Richieri et al. (1996) J. Biol. Chem. vol. 271: pages 11291–11300) provided an average and standard deviation of 2.8 nM and 0.7 nM. The difference in values obtained for the 2 probes is due in part to the decrease in [FFA$_u$] with decreasing temperature and to the greater sensitivity of the ADIFAB probe to factors in plasma, such as hemoglobin, that preferentially absorb the shorter wavelength fluorescence of the ADIFAB as compared to the ADIFAB2 probe.

Measurements of [FFA$_u$] in patients with a wide range of diseases reveal that, with the exception of patients with cerebral or cardiac ischemia and possibly sepsis, the distribution of [FFA$_u$] for this disease population is quite similar to the distribution of normal asymptomatic individuals. In contrast to these results, patients with cerebral ischemia reveal significantly elevated [FFA$_u$].

Blood samples are obtained from patients presenting at several different hospitals with possible stroke. The blood specimens are drawn for each patient at one or more times during their hospitalization. Results of [FFA$_u$] measurements on samples taken at presentation (between 2 and 5 hours after first symptoms) reveal a distribution that is shifted to significantly higher levels as compared to asymptomatic individuals. These results indicate that measurements of [FFA$_u$] provide an early and accurate diagnosis of ischemic stroke in humans.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of determining the presence of stroke in a mammal comprising the steps of:
   providing a body fluid sample selected from the group consisting of whole blood, serum and plasma from a mammal exhibiting symptoms consistent with ischemic stroke;
   mixing the sample with an aqueous solution and with a reagent comprising a fatty acid binding protein labeled with a fluorescent moiety, wherein said reagent exhibits a first fluorescence in an aqueous solution and a measurably different second fluorescence in an aqueous solution when said fatty acid binding protein is bound to a fatty acid;
   measuring said second fluorescence after said body fluid sample is mixed with said aqueous solution and said reagent to determine a concentration of unbound free fatty acid in said body fluid sample; and
   comparing the concentration of unbound free fatty acid in the body fluid sample to a threshold value determined from a normal population that does not have stroke, wherein an elevated value indicates the presence of stroke.

2. A method of determining the presence of stroke in a patient presenting with symptoms consistent with stroke comprising:
   measuring unbound free fatty acid levels in a body fluid sample selected from the group consisting of whole blood, serum and plasma from said patient;
   comparing the measured level of unbound free fatty acid to a threshold level of unbound free fatty acid, wherein said threshold level is determined from measuring unbound free fatty acid in body fluid of a normal population that does not have stroke; and
   determining whether the unbound free fatty acid level from the patient's body fluid sample is elevated relative to the threshold level of unbound free fatty acids from the normal population, wherein said relative elevation indicates the presence of stroke.

3. The method of claim 2, wherein said measuring step further comprises the steps of:
   mixing said body fluid sample with an aqueous solution and with a reagent comprising a fatty acid binding protein labeled with a fluorescent moiety, wherein said reagent exhibits a first fluorescence in an aqueous solution and a measurably different second fluorescence in an aqueous solution when said fatty acid binding protein is bound to a fatty acid; and
   measuring said second fluorescence after said body fluid sample is mixed with said aqueous solution and said reagent to determine a concentration of unbound free fatty acid in said body fluid sample.

4. The method of claim 2, wherein said measuring step of said second fluorescence is performed at a wavelength that differs from a wavelength at which said reagent exhibits said first fluorescence.

5. The method of claim 4, wherein said wavelength for measuring said second fluorescence is about 420 nm to about 460 nm, and wherein said wavelength at which said reagent exhibits said first fluorescence is about 495 nm to about 560 nm.

6. The method of claim 3, further comprising the steps of:
   measuring total free fatty acid and albumin in said blood sample; and
   determining a ratio of said total free fatty acid and said albumin.

7. The method of claim 3, wherein said fatty acid binding protein is a rat intestinal fatty acid binding protein, a human adipocyte fatty acid binding protein, or a rat heart fatty acid binding protein, and wherein said fluorescent moiety is acrylodan, danzyl aziridine, 4-[N-[(2-iodoacetoxy)ethyl]-N-methylamino]-7-nitrobenz-2-oxa-1,3-diazole ester (IANBDE), or 4-[N-[(2-iodoacetoxy)ethyl]-N-methylamino]-7-nitrobenz-2-oxa-1,3-diazole (IANBDA).

8. The method of claim 3, wherein said reagent in said mixing and measuring steps is a fatty acid binding protein labeled with acrylodan, wherein said fatty acid binding protein is a mutant protein comprising a rat intestinal fatty acid binding protein having a cysteine at residue 27, 81, 82, or 84, or an alanine at residue 72, or a rat heart fatty acid binding protein having a lysine at residue 27.

9. The method of claim 3, wherein said reagent in said mixing and measuring steps is a rat intestinal fatty acid binding protein labeled with acrylodan.

10. The method of claim 9, wherein said reagent is a rat intestinal fatty acid binding protein labeled with acrylodan and having an alanine at residue 72.

11. The method of claim 3, wherein the concentration of the unbound free fatty acid greater than 2 standard deviation units above an average value of the concentration of the unbound free fatty acid determined from a non-ischemic population is indicative of stroke.

12. The method of claim 3, wherein the concentration of the unbound free fatty acid greater than about twice an average value of the concentration of the unbound free fatty acid determined from a non-ischemic population is indicative of stroke.

13. The method of claim 2, wherein said measuring step further comprises the steps of:
   mixing said body fluid sample with an aqueous solution and with a reagent comprising albumin labeled with a fluorescent moiety selected from the group consisting of 7-hydroxycoumarin and anthraniloyl, wherein said reagent exhibits a first fluorescence in an aqueous solution and a measurably different second fluorescence in an aqueous solution when said albumin is bound to a fatty acid; and
   measuring said second fluorescence after said body fluid sample is mixed with said aqueous solution and said reagent to determine a concentration of unbound free fatty acid in said body fluid sample.

14. A method for diagnosing ischemic stroke, comprising:
   identifying a patient presenting symptomology consistent with ischemic stroke;
   obtaining a body fluid sample selected from the group consisting of whole blood, serum and plasma from the patient;
   measuring a level of unbound free fatty acid in the sample; and
   ascertaining whether the measured level of unbound free fatty acid is sufficiently elevated to be indicative of ischemic stroke.

15. The method of claim 14, further comprising:
   administering thrombolytic therapy to the patient when the measured level of unbound free fatty acid is indicative of ischemic stroke.

* * * * *

UNITED STATES PATENT AND TRADEMARK OFFICE
CERTIFICATE OF CORRECTION

PATENT NO. : 7,202,089 B2
APPLICATION NO. : 10/243565
DATED : April 10, 2007
INVENTOR(S) : Alan Kleinfeld It is certified that error appears in the above-identified patent and that said Letters Patent is hereby corrected as shown below:

On the Title Page, Item (56) Other Publications, Line 20, "Flourescent Probe ADIFAB,"" should be changed to --Fluorescent Probe ADIFAB,"--

On the Title Page 2, Item (56) Other Publications, Line 4, "Samanta, et a." should be changed to --Samanta, et al.--

Column 3, Lines 28-29, "-N-methy-lamino]-7-nitrobenz-2-oxa-" should be changed to -- -N-methyl-amino]-7-nitrobenz-2-oxa- --

Column 10, Line 63, "and $TN_F\alpha$." should be changed to --and $TNF_\alpha$.--

Column 14, Line 3, "diagnosing ischemic stroke," should be changed to --determining the presence of ischemic stroke,--

Signed and Sealed this

Thirty-first Day of July, 2007

JON W. DUDAS
*Director of the United States Patent and Trademark Office*